United States Patent [19]

Pyke et al.

[11] Patent Number: 4,895,017
[45] Date of Patent: Jan. 23, 1990

[54] APPARATUS AND METHOD FOR EARLY DETECTION AND IDENTIFICATION OF DILUTE CHEMICAL VAPORS

[75] Inventors: Stephen C. Pyke, Monroe; Harold E. Hager, Bellevue, both of Wash.

[73] Assignee: The Boeing Company, Seattle, Wash.

[21] Appl. No.: 300,367

[22] Filed: Jan. 23, 1989

[51] Int. Cl.$^4$ ............................................. G01N 31/06
[52] U.S. Cl. ............................................................. 73/23
[58] Field of Search ................... 73/23, 579, 26, 27 R; 422/88, 98

[56] References Cited

U.S. PATENT DOCUMENTS

| 4,312,228 | 1/1982 | Wohltjen | 73/23 |
| 4,361,026 | 11/1982 | Mueller et al. | 73/23 |
| 4,502,321 | 3/1985 | Zuckerman | 73/23 |
| 4,596,697 | 6/1986 | Ballato | 73/23 |
| 4,598,224 | 7/1986 | Ballato | 73/23 |

Primary Examiner—Michael J. Tokar
Assistant Examiner—Louis M. Arana
Attorney, Agent, or Firm—Christensen, O'Connor, Johnson & Kindness

[57] ABSTRACT

A detector and method for identifying a chemical vapor and determining its concentration in the ambient atmosphere. The chemical detector apparatus (120) preferably includes a plurality of surface acoustic wave (SAW) devices (10), each including a piezoelectric substrate (20), one-half (32) of which is coated with a selected polymer. The polymer characteristically absorbs one or more of a group of chemical vapors. Diffusion of a chemical vapor into the polymer increases its mass and proportionately changes the resonant frequency of the SAW device. A microcomputer control (186) is operative to determine a predicted time constant (or rate) for diffusion and a predicted equilibrium concentration of the chemical vapor within the polymer coating of the SAW device and to identify the chemical vapor and its relative concentration in the ambient atmosphere using the predicted values for these parameters long before the SAW device has reached equilibrium with the chemical vapor.

30 Claims, 7 Drawing Sheets

APPARATUS AND METHOD FOR EARLY DETECTION AND IDENTIFICATION OF DILUTE CHEMICAL VAPORS

TECHNICAL FIELD

The present invention generally pertains to a chemical vapor sensor and a method for sensing and identifying chemical vapors, and more particularly, to a sensor and method in which a physical parameter associated with the sensor changes in a defined manner upon exposure to the chemical vapor, permitting its identification.

BACKGROUND OF THE INVENTION

Unless provided with a fully equipped chemical laboratory, detection and identification of relatively dilute ambient concentrations of chemical vapors can represent a formidable task. Chemical vapor analyses are typically sensitive to only very specific vapors, generally producing a positive identification of a vapor through an irreversible chemical reaction. Automated apparatus to detect and identify chemical vapors have generally not been commercially available. The few portable chemical vapor detectors previously developed have required a relatively high concentration of a vapor in air or a relatively long exposure time to make a positive identification.

Chemical sensors have recently been developed that do not chemically react with a substance, but instead, physically change upon exposure to it. These chemical sensors typically include a polymer selected for its affinity to dissolve or absorb a group of related chemical vapors. As the chemical vapor dissolves or diffuses into the polymer, it causes a characteristic change in a parameter associated with the sensor. Perhaps the most fully developed of this type of chemical sensor is the surface acoustic wave (SAW) device. SAW devices suitable for use as chemical vapor sensors are readily available, for example, from a company that pioneered their development, Microsensor Systems, Inc., Fairfax, Virginia.

A method and apparatus for using a SAW device to detect a vapor is disclosed in U.S. Pat. No. 4,312,228. As described therein, the SAW device comprises a piezoelectric element having a surface coated with a material selected to interact with the chemical to be detected. Electrodes on the piezoelectric element are excited by a high frequency oscillator, producing a surface acoustic wave. Interaction of the chemical with the material coating the element alters one or more properties of the wave, and the electrodes on the piezoelectric element detect the altered wave, producing an electrical signal. The electrical signal is used to identify the chemical. While the material coating the surface of the element may be selected to chemically interact with the vapor in certain applications, to achieve reversible interaction, it is preferable to select a material for the coating that only physically interacts with the chemical.

The coating applied to a SAW device is typically a polymer selected for its characteristic interaction with the specific vapor or group of vapors to be detected. For example, fluoropolyol has been used as such a coating, since it absorbs a variety of chemical vapors. The absorption of a chemical vapor by the polymer coating of the SAW device increases the mass of the coating, and proportionally reduces the frequency of the surface acoustic wave propagating through the device. By monitoring the frequency of the surface acoustic wave, the absorption of a chemical substance into the polymer can be measured. Comparison of the measured absorption to the known characteristic solubility of the chemical vapor (or at least the class of chemical vapors) to which the sensor is exposed allows the determination of the ambient vapor concentration.

To qualitatively identify a specific chemical vapor, pattern recognition techniques are applied to an array of SAW devices that are each coated with different polymers. This method is described in a paper entitled, "Correlation of Surface Acoustic Wave Device Coating Responses With Solubility Properties and Chemical Structure," by D. S. Ballentine, Jr., S. L. Rose, J. W. Grate, and H. Wohltjen, published in Analytical Chemistry, Vol. 58, p. 3058, December 1986. As detailed therein, an evaluation was made using 12 SAW devices, coated with different polymer materials. The sensors were exposed to filtered air for one minute to establish a baseline response, followed by successive alternating exposures to a selected chemical vapor and the filtered air, each exposure lasting for approximately two minutes. The mass of the polymer coating increased exponentially as the chemical vapor was absorbed during each exposure, reaching an equilibrium level that varied as a function of the vapor concentration and of the affinity of each polymer coating to absorb that particular chemical vapor. During exposure to clean, filtered air, the chemical vapor exponentially desorbed from the polymer coating.

The normalized equilibrium concentration of a given chemical vapor in the polymer coating of each of the 12 SAW devices was evaluated using an eigenvector analysis technique. This analysis technique established sensor response patterns defining clusters for the response related to two classes of chemical vapors used in the test. It was found that four coatings, i.e., four different SAW devices, were sufficient to identify which of the two classes of chemical vapors were present, with almost 100% certainty.

There are two problems with the procedures used for identifying chemical substances in the above-described test. The prior method described relies upon determining the equilibrium concentration of a chemical vapor absorbed into the selected coating on a SAW device, providing only a single datum for the exposure of each device to a given chemical vapor. Furthermore, when the SAW device is exposed to very dilute concentrations of a chemical vapor, the time required for the chemical to absorb into the polymer coating to a level approaching its equilibrium concentration may be relatively long, for example, in excess of 15 minutes. In some applications, particularly those involving detection of harmful chemical vapors using a SAW device, it is critical that the chemical vapor be detected (and identified) before personnel in the area are adversely affected. The opposite problem arises where a chemical vapor is so highly concentrated that it saturates the polymer coating, making the SAW device insensitive to further exposure and use for an extended period of time.

Accordingly, it is an object of the present invention to rapidly detect a chemical substance present in relatively low concentrations and determine its ambient concentration. It is a further object to identify the chemical substance, or at least determine that it is from a known group of chemical substances. Yet a further object is to detect and/or identify a chemical substance based upon its predicted equilibrium concentration and its predicted time constant for diffusion into the coating of a sensor. Still a further object is to identify a chemical substance present in relatively high concentration, before it saturates the sensor. These and other objects and advantages of the present invention will be apparent from the attached drawings and the Description of the Preferred Embodiments that follows.

SUMMARY OF THE INVENTION

In accordance with the present invention, apparatus is provided for rapidly detecting and identifying a chemical substance. The apparatus includes a sensor having a surface which is exposed to the chemical substance and comprises a material selectively absorptive of a group of chemical substances of which said chemical substance is a member. A physical parameter associated with the surface of the sensor changes as the quantity of the chemical substance absorbed by diffusion into the material changes.

Monitoring means, coupled to the sensor, are operative to monitor the change in the physical parameter associated with the surface due to absorption of the chemical substance, producing an electrical signal indicative of the change. Connected to the monitoring means are analysis means, functioning to determine a predicted time constant for diffusion of the chemical substance into the material and a predicted equilibrium concentration of the chemical substance in the material as a function of the electrical signal, well before the concentration of the chemical substance in the material asymptotically approaches equilibrium. The chemical substance is identified from the group of chemical substances by identification means, based on both its predicted time constant for diffusion and predicted equilibrium concentration, which are generally characteristic of it and different than those of other chemical substances of that group.

The sensor may preferably comprise a surface acoustic wave device having at least one surface coated with the material selectively absorptive of the group of chemical substances. Absorption of the chemical substance into the material changes its mass; and the physical parameter is thus the frequency of a surface acoustic wave propagating along the coated surface of the surface acoustic wave device. The frequency of the surface acoustic wave decreases as the mass of the coating increases due to absorption of the chemical substance.

The material coating the one surface of the surface acoustic wave device comprises a polymer. A plurality of spaced apart electrodes are disposed on the surface acoustic wave device, and the polymer is disposed between pairs of the electrodes. Means are also provided to excite the surface acoustic wave device with a periodically varying signal. The monitoring means used with the surface acoustic wave device comprise a high-speed counter connected to determine the frequency of the surface acoustic wave propagating through the material. A sampling rate is used that is substantially faster than an expected rate for the concentration of chemical substance in the material to reach equilibrium. The electrical signal produced by the sensor indicates the change in frequency due to absorption of the chemical substance in the material coating the one surface of the surface acoustic wave device.

Optionally, the apparatus may include a concentrator, operative to increase the relative concentration of the chemical substance to which the surface is exposed.

A plurality of other sensors, each having a surface exposed to the chemical substance and each comprising a different material selectively absorptive of a different group of chemical substances, may also be used. The identification means are then operative to identify the chemical substance as a function of predicted rates of diffusion and predicted equilibrium concentrations determined by the analysis means for all of the sensors.

The sensor may alternatively comprise a chemical field effect transistor, including a semiconductor coated with the material, the diffusion of the chemical substance into the material acting to modulate the flow of free charge carriers within the material. In this type sensor, the physical parameter comprises the conductivity between a source and a drain of the chemical field effect transistor, due to a localized electric field in the material caused by diffusion of the chemical vapor into the material.

As a further alternative, the sensor may comprise a chemical resistor that changes impedance as the chemical vapor diffuses into the material. The physical parameter of this sensor comprises the resistance of the chemical resistor.

A method, including steps generally corresponding to the functions implemented by elements of the apparatus described above, is a further aspect of the present invention.

DESCRIPTION OF THE PREFERRED EMBODIMENTS

Figure 1:
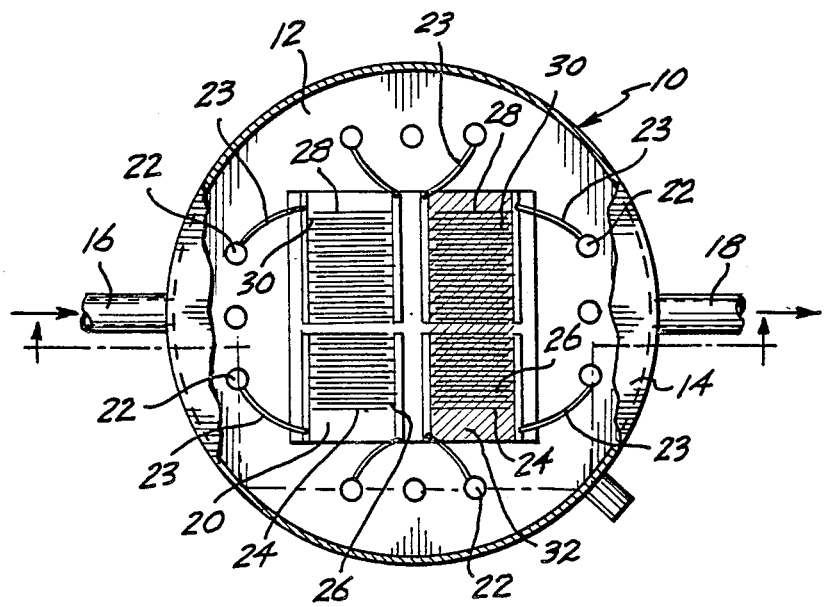
FIG. 1 schematically illustrates a surface acoustical wave sensor, with its cover partially cut away.

While the present invention is applicable to other types of chemical sensors, the preferred embodiment uses a surface acoustic wave (SAW) device, as shown generally at reference numeral 10 in FIG. 1. SAW device 10 is housed in a modified type TO-8 integrated circuit package, including a base 12 and a cover 14. Cover 14 is modified to include an inlet port 16 and an outlet port 18, through which the chemical vapor to be identified is conveyed for exposure to SAW device 10. Cover 14 has been partially cut away in FIG. 1, to facilitate disclosure of the chemical vapor sensor contained therein. This sensor includes a piezoelectric substrate 20, mounted in the center of base 12 and surrounded by a plurality of connector pins 22, which extend outwardly through the base. Piezoelectric substrate 20 is divided longitudinally into two SAW sensors. Leads 23 connect eight of connector pins 22 to selected interdigital electrodes 24, 26, 28, and 30 on each of the sensors. Interdigital electrodes 24 are paired with interdigital electrodes 26, each extending part way across one-half of piezoelectric substrate 20, i.e., across each of the SAW sensors, in parallel alignment, but not in contact with one another. Similarly, interdigital electrodes 28 and 30 are paired together and extend over one-half of the other end of piezoelectric substrate 20 on both SAW sensors, in parallel relationship to each other.

As shown in FIG. 1, the SAW device on the right half of piezoelectric substrate 20 (the cross-hatched area identified by reference numeral 32) is coated with a polymer selected for its characteristic affinity to absorb a group of related chemical substances. Examples of such polymers include polyethylene maleate, fluoropolyol, collodion, abietic acid, polyacrylic acid, polystyrene, polyvinyl pyrollidone, polyethylene imine, polyethylene adipate, polychloroprene, chlorinated rubber, carbowax 20M, polyisobutylene, polycaprolactone, polyepichlorohydrin, ethyl cellulose, polyhydroxypropyl methacrylate, and other polymers known to absorb specific chemical substances. The SAW sensor on the left half of piezoelectric substrate 20 is not coated with such a polymer, but may be coated with a vapor impermeable material.

Figure 2:
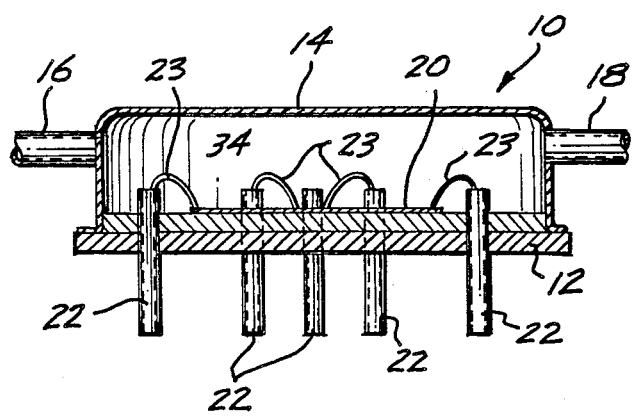
FIG. 2 is a plan view, schematically illustrating the SAW sensor of FIG. 1.

FIG. 2 shows a chamber 34 disposed above piezoelectric substrate 20, into which air carrying a chemical vapor flows from inlet port 16, the chemical vapor thus coming into contact with the polymer coating. The chemical vapor diffuses into the polymer coating, increasing its mass, the time constant for diffusion and solubility of the chemical vapor in the polymer coating depending upon the specific polymer used. The uncoated (or vapor impermeable) SAW sensor on the left half of the piezoelectric substrate functions as a reference sensor, and is unaffected by the chemical vapor.

Figure 3:
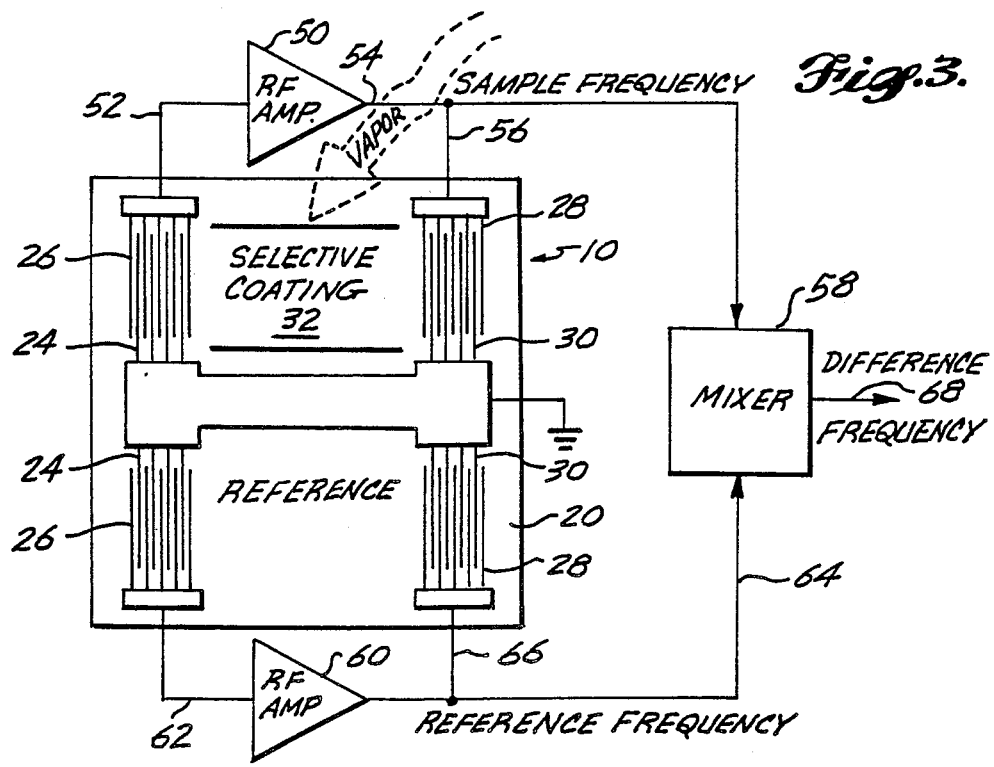
FIG. 3 is a simplified schematic block diagram of a SAW sensor circuit.

SAW device 10 is schematically shown in FIG. 3, along with other portions of a circuit used to produce an output signal indicative of the mass of chemical substance absorbed or diffused into the polymer coating of the device. The manner in which a SAW device operates is well known to those of ordinary skill in the art, and therefore need not be disclosed in detail. The piezoelectric substrate of SAW device 10 functions as a mechanically resonant structure through which Rayleigh surface waves propagate. In each SAW sensor, the pairs of interdigital electrodes are photolithographically patterned at both ends of the piezoelectric substrate. Interdigital electrodes 24 and 26 are excited with a radio frequency sinusoidal voltage, generating Rayleigh waves that travel across the surface of each sensor for reception by interdigital electrodes 28 and 30. Since most of the energy of the Rayleigh wave is constrained to be at the surface of the SAW sensor, it interacts with any material that is in contact with the surface, such as the polymer coating in area 32. As the mass of the coating changes due to absorption of a chemical substance, the mechanical modulus of the surface is altered and the velocity of the Rayleigh wave changes proportionally. Changes in the Rayleigh wave velocity appear as shifts in the resonant frequency of the device.

Since both the reference SAW sensor and the SAW sensor selectively coated with the polymer are formed on the same piezoelectric substrate in SAW device 10, drift in the resonant frequency of the selectively coated SAW sensor due to changes in ambient temperature and pressure is compensated. Comparison of the resonant frequency of the reference half and the selectively coated half of piezoelectric substrate 20 is accomplished by mixing their resonant frequencies.

As shown in FIG. 3, and RF amplifier 50 is connected through a lead 52 to interdigital electrodes 26, interdigital electrodes 24 being commonly grounded. The output of RF amplifier 50 is connected through a lead 56 to interdigital electrodes 28 on the polymer-coated half of piezoelectric substrate 20, and the amplified resonant frequency of that half appears on a lead 54 and is input to a mixer 58. Similarly, the input of an RF amplifier 60 is connected via a lead 62 to interdigital electrodes 26 on the reference half of piezoelectric substrate 20. The resonant frequency of the SAW sensor is amplified by RF amplifier 60 and is output over a lead 64. The amplified output of RF amplifier 60 is also connected to interdigital electrode 28 through a lead 66. Lead 64 input to mixer 58, providing the reference resonant frequency for comparison to the resonant frequency from the polymer-coated side of SAW device 10. The difference frequency between the two signals on lead 54 and 64 is output from mixer 58 over a lead 68.

SAW devices such as that shown in FIGS. 1–3 are capable of resolving less than one nanogram change in mass of polymer-coated area 32, due to its absorption of a chemical substance. For example, in a SAW device having a nominal resonant frequency of 158 megahertz, absorption of one nanogram mass by the polymer coating would cause the resonant frequency to shift by approximately 360 Hertz, a change that is well above its rated signal-to-noise ratio.

Figure 6:
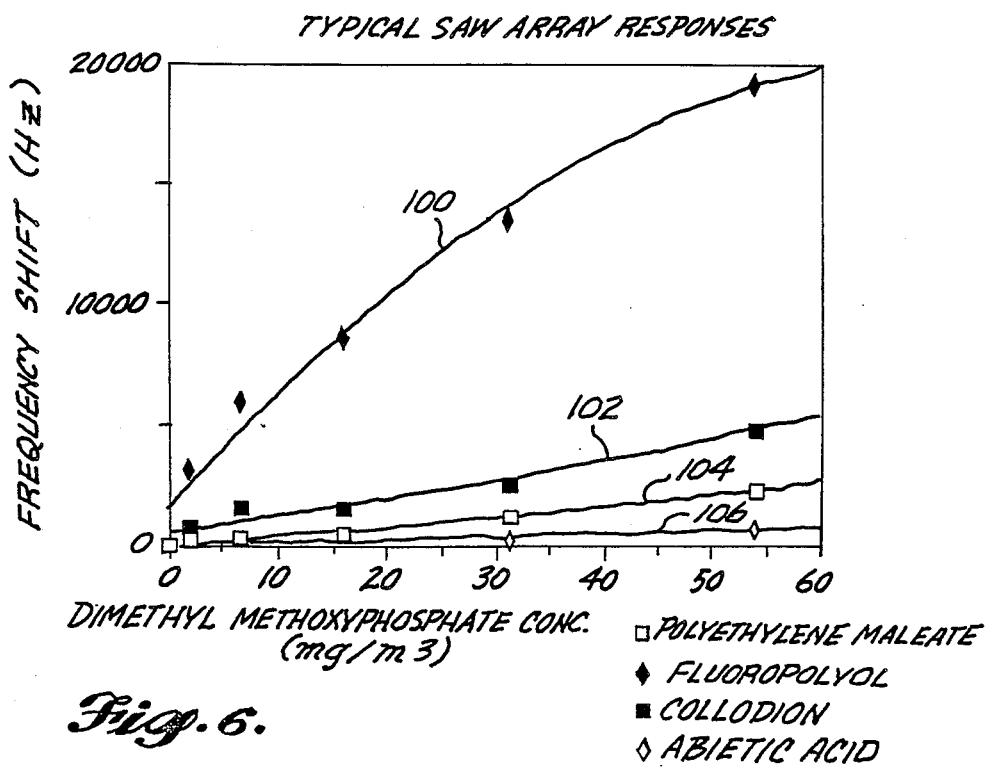
FIG. 6 illustrates the equilibrium response of four SAW sensors, that are each coated with different polymer material, with respect to varying concentrations of dimethyl methylphosphonate vapor.

The sensitivity of a given SAW device to a specific chemical substance, of course, depends on the particular polymer coating used and the chemical substance to which it is exposed. FIG. 6 graphically illustrates differences in sensitivity for exposure to various dimethyl methylphosphonate concentrations, for each of four SAW devices having different polymer coatings, including polyethylene maleate (curve 100), fluoropolyol (curve 102), collodion (curve 104), and abietic acid (curve 106). Clearly, polyethylene maleate is much more "sensitive" to (i.e., has a greater affinity to dissolve) dimethyl methylphosphonate than the other three polymers, since it absorbs a substantially greater mass of the chemical at the various equilibrium concentrations shown. Conversely, abietic acid shows the least "sensitivity," absorbing very little of the dimethyl methylphosphonate, even at relatively higher concentrations of the vapor in air.

As noted above, SAW devices have been used in prior art chemical sensors to detect the presence of a particular chemical substance or group of chemical substances. In the past, however, only the change in resonant frequency at an equilibrium concentration of the chemical substance in the polymer has been used to identify the chemical substance to which the SAW device is exposed. As previously explained, a plurality of SAW devices having different polymer coatings, each with a characteristic affinity to absorb different chemical substances may be used to discriminate amongst a plurality of possible chemical substances, in identifying the chemical substance in question.

The only physical parameter used in prior art identification methods has been the equilibrium concentration of the chemical substance absorbed into the polymer coating, measured by monitoring the change in resonant frequency to determine its value after it has stabilized following a step change in the ambient concentration of the chemical substance. However, another characteristic parameter of the absorption process can be used to identify the chemical substance and to determine its concentration in the ambient, which has not been used in prior methods. That characteristic parameter is the time for diffusion or rate at which the chemical substance absorbed by the selected polymer approaches its equilibrium concentration within the polymer coating.

Figure 7:
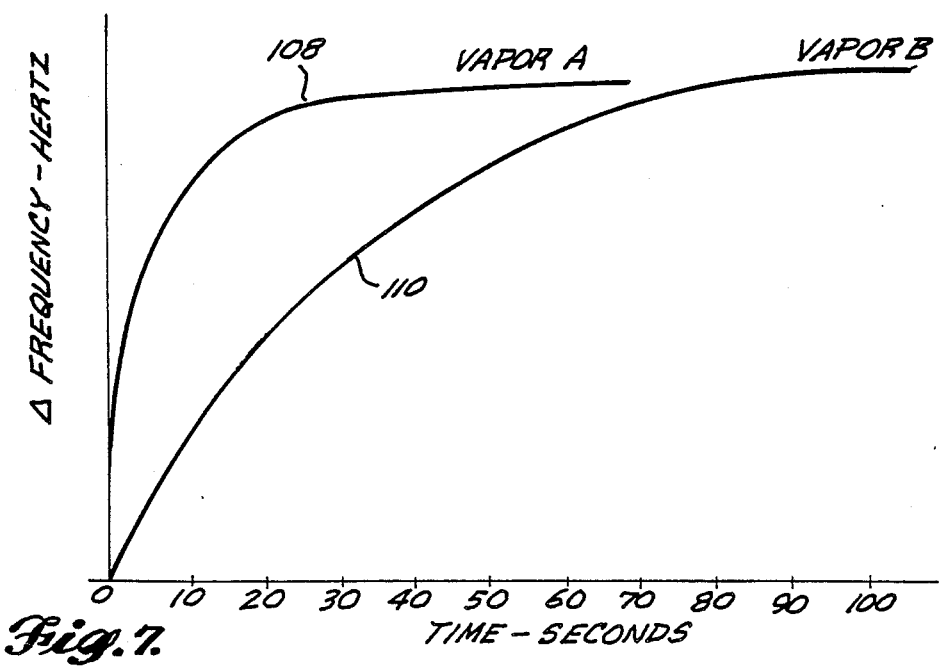
FIG. 7 is a graph showing the relative rate of change of the resonant frequency of a SAW sensor with respect to two different chemical vapors.

FIG. 7 illustrates the time rate of change of the resonant frequency of a SAW device when exposed to a chemical vapor A, represented by curve 108, and when exposed to a chemical vapor B, represented by curve 110. Both curves 108 and 110 asymptotically approach approximately the same value, indicating that the equilibrium mass loading of chemical vapors A and B within the polymer coating on the SAW device are approximately the same. (Since vapors A and B likely have different molecular weights, their equilibrium concentrations in the polymer coating will be different.) However, curve 108 has a much steeper slope, i.e., chemical vapor A diffuses into the polymer coating much more rapidly than chemical vapor B, and thus exhibits a shorter time constant for diffusion. For purposes of this disclosure and the claims, the "time constant for diffusion" is defined as the time required for a chemical substance to reach about 37% of its equilibrium concentration within the polymer coating after it is first exposed to a step change in the ambient concentration of the chemical substance. A related term, the "rate constant," is simply the reciprocal of the time constant for diffusion. It will be understood that either the time constant for diffusion or the rate constant are characteristic of an important parameter of the diffusion process and in that respect, may be used interchangeably and treated as equivalents within the scope of the claims. This parameter provides additional information about the diffusion process that has not been previously considered. Using both the time constant for diffusion of a chemical substance into the polymer coating and the equilibrium concentration of the chemical substance within the coating, identification of the chemical substance and its concentration in the environment can be determined more readily, and with much less uncertainty than by using only the equilibrium concentration. In addition, a chemical substance can be detected and identified at much lower ambient concentration of the chemical substance.

Figure 4:
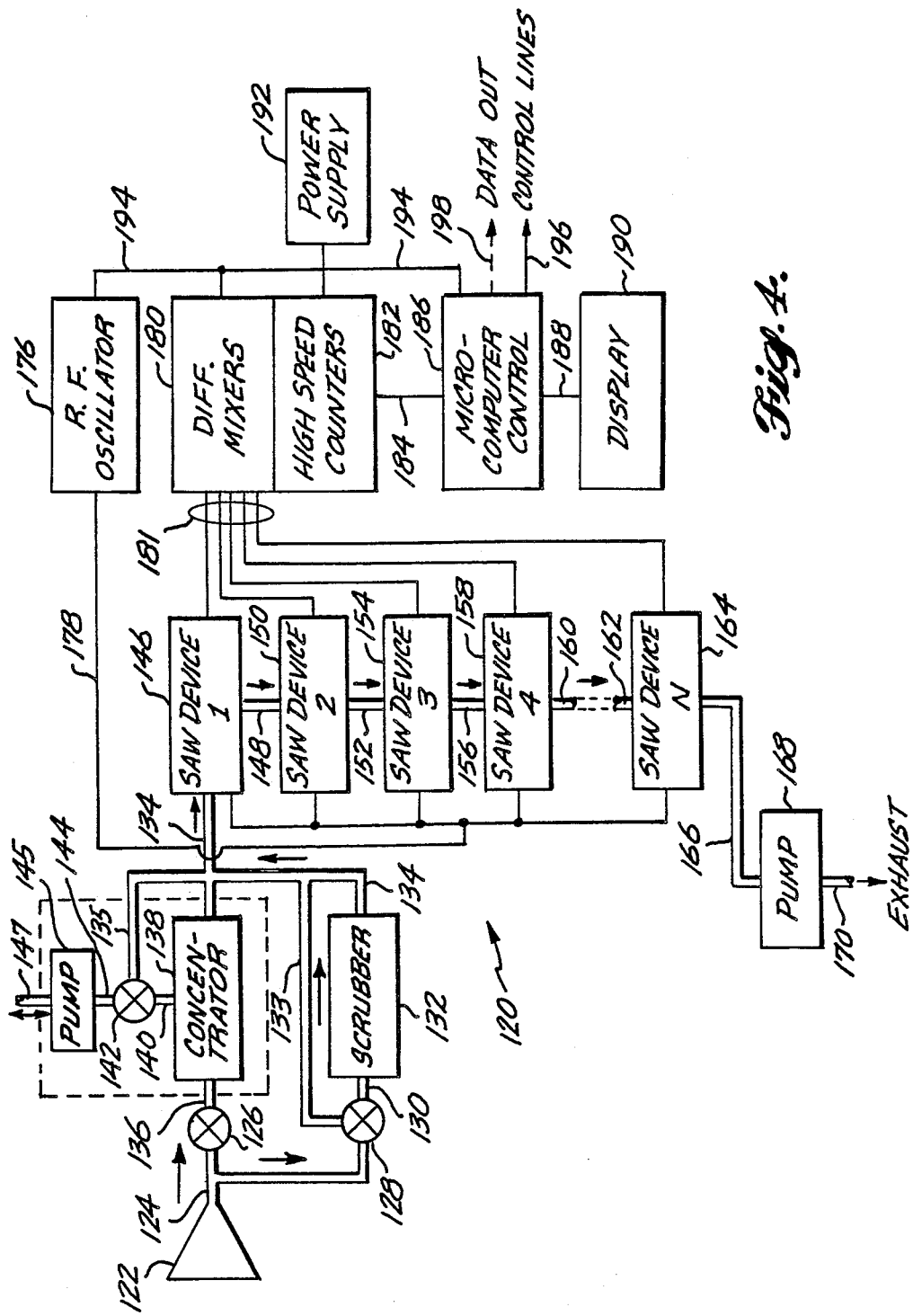
FIG. 4 is a block diagram of apparatus for identifying chemical vapors and determining their concentration in ambient air.

Apparatus for detecting and identifying chemical vapors and their relative concentration in the ambient atmosphere is shown in FIG. 4, generally represented at reference numeral 120. The apparatus includes an inlet cone 122 through which is drawn a sample of ambient air containing a chemical vapor to be identified. Air entering the inlet cone passes through a line 124, which is connected to both a solenoid valve 126 and a three-way solenoid valve 128. One outlet of three-way solenoid valve 128 is connected through a line 130 to the inlet of a scrubber 132, which may comprise, for example, an activated charcoal filter that is operative to remove chemical vapors from the air sample drawn through inlet cone 122. The other outlet of three-way solenoid valve 128 bypasses scrubber 132 through a line 133, which is connected to a line 134. The outlet of scrubber 132 is connected through line 134 to the inlet of a SAW device 146.

The outlet of solenoid valve 126 is connected through a line 136 to the inlet of an optional concentrator 138. If optional concentrator 138 is not used, line 136 may be capped. Optional concentrator 138 is connected through a line 140 to a three-way solenoid valve 142, one outlet of which connects to line 134 through a line 135, the other outlet being connected to the inlet of a pump 145 through a line 144. Pump 145, which is only used when optional concentrator 138 is provided, includes an exhaust line 147. Operation of the optional concentrator is described below.

SAW device 146 is the first in a plurality of SAW devices connected in series or cascade fashion. Accordingly, the outlet port of SAW device 146 connects through a line 148 to the inlet port of a SAW device 150, the second in the plurality of cascaded SAW devices. Similarly, a line 152 connects SAW device 150 to a SAW device 154, and a line 156 connects SAW device 154 to a SAW device 158. A total of N different SAW devices, the last of which is represented in FIG. 4 by a SAW device 164, are serially connected in cascade fashion. Lines 160 and 162 connect the last SAW devices to the preceding ones. The output port of the Nth SAW device 164 connects through a line 166 to the inlet of a pump 168, having an exhaust line 170. (Pump 145 may be eliminated if pump 168 is appropriately connected to line 144, e.g., by extending line 144 to a "T" in line 166). Alternatively, the N SAW devices can be connected in parallel. In the preferred embodiment, N is equal to four. Generally, the number of SAW devices used depends on the variety of chemical substances to be detected and identified.

SAW devices 146 through the Nth SAW device 164 are driven by an RF oscillator 176, which includes an RF amplifier (not separately shown) for each of the two SAW sensors in each of the SAW devices. RF oscillator 176 and the RF amplifiers are connected to the SAW devices by leads 178. The output signals from the SAW devices are conveyed to differential mixers 180 over leads 181. A separate differential mixer is provided for each of SAW devices 1 through N, each differential mixer producing a difference frequency that is input to high-speed counters 182. High-speed counters 182 sample the difference frequency from each SAW device approximately 10 times per second, producing a digital signal, which is output over leads 184 to a microcomputer control 186. Microcomputer control 186 monitors the digital signal supplied from high-speed counters 182 and computes data comprising a predicted time constant for diffusion of a chemical substance into the polymer coating on each of the SAW devices 1 through N, and a predicted equilibrium concentration of the chemical substance in the polymer coating for each SAW device. The computed values are calculated for each data point and converge on equilibrium more quickly than the measured frequency change.

In addition, microcomputer control 186 implements a pattern matching algorithm to identify the chemical vapor sampled by the apparatus at inlet cone 122 and its relative concentration in the ambient atmosphere, by comparing the predicted time constant for diffusion and predicted equilibrium concentration from each SAW device to values in a look-up table stored in its nonvolatile memory. The results of implementing the pattern matching algorithm are shown on a display 190. Display 190 may comprise a conventional cathode ray tube or a liquid crystal display on which the chemical vapor is specifically identified by name and its concentration in the ambient atmosphere indicated. In addition, data produced by high-speed counters 182 or computed data developed by microcomputer control 186 may optionally be output over data lines 198 to an external data reduction system or other computer.

A power supply 192 is connected through leads 194 to each of the components of apparatus 120 that require electrical power. Power supply 192 is of generally conventional design, and may comprise either a DC battery driven supply or a DC supply powered with AC line current.

Microcomputer control 186 controls the various components of apparatus 120, such as solenoid valves 126, 128, and 142, using control signals transmitted over control lines 196. Similarly, pumps 168 and 145 are energized in response to such control signals to draw vapor through the SAW devices and through optional concentrator 138 during a predetermined measurement cycle.

Figure 5:
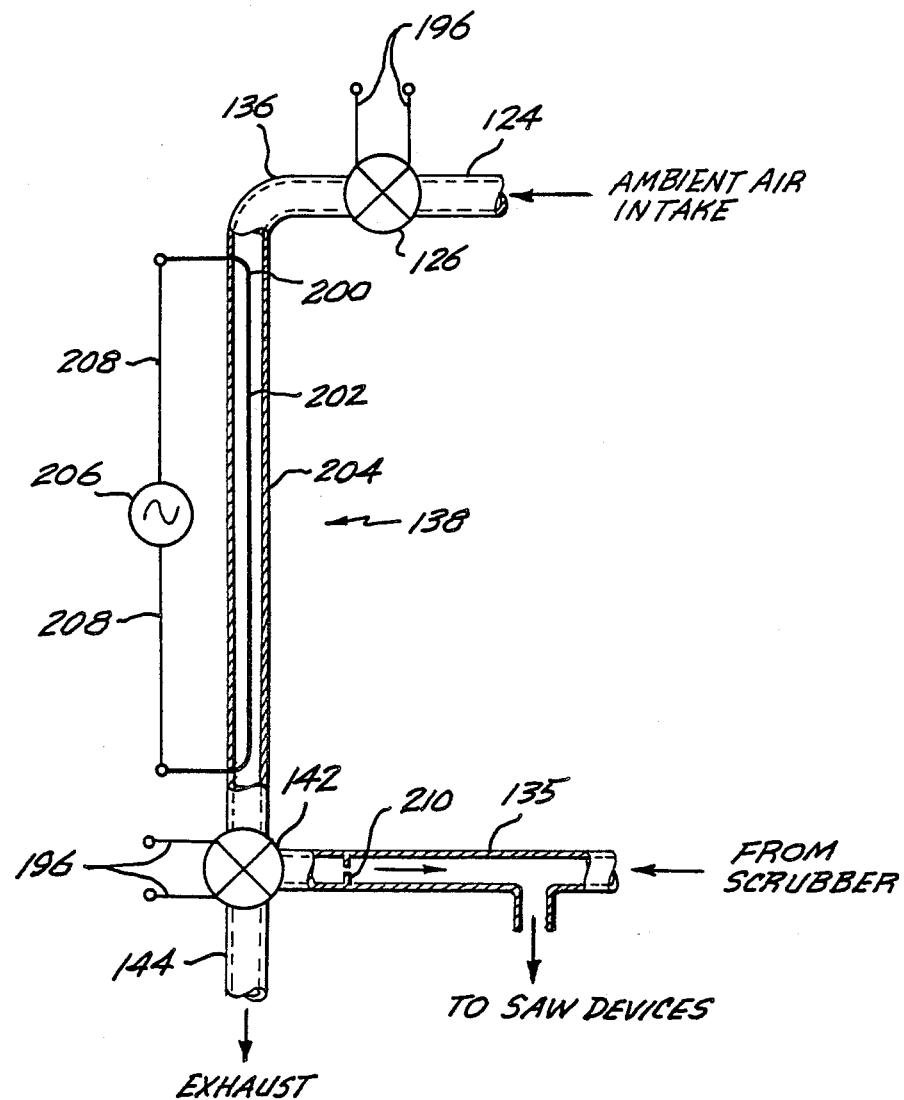
FIG. 5 schematically illustrates a concentrator used to increase the relative concentration of a chemical vapor to which a sensor is exposed.

Details of optional concentrator 138 are shown in FIG. 5. Concentrator 138 preferably includes a helically coiled platinum or nichrome wire 200, which extends longitudinally along a ¼ inch diameter flow passage 204, having a volume of 10–30 cm$^3$. Wire 200 is covered with a polymer coating 202 along substantially all of its length, internal to flow passage 204. The total surface area of polymer coating 202 is preferably a minimum of about 2 cm$^2$. The ends of wire 200 pass sealingly through the walls of flow passage 204, and are connected to a power source 206 by leads 208. Power source 206 is controlled by microcomputer control 186 and is operative to pass an electrical current through wire 200, causing it to be selectively heated at two different rates. Polymer coating 202 on wire 200 is characterized by its affinity to absorb the full range of chemical substances of interest, and may, for example, comprise fluoropolyol. As polymer coating 202 is heated by the electrical current passing through wire 200, the elevated temperature causes it to desorb the chemical vapor so that the chemical vapor may be detected by the SAW devices at a higher concentration than present in ambient air. Three-way solenoid valve 142 is selectively actuated to permit fluid flow from solenoid valve 126 to pass through concentrator 138, drawn by pump 145 (shown in FIG. 4), for exhaust to the ambient atmosphere, or alternatively, to divert flow from concentrator 138 through line 135. Fluid flow through line 135 is restricted by a flow orifice 210, disposed upstream of the SAW devices.

For operation of the preferred embodiment of apparatus 120, a two-minute measurement cycle is used. During the first 105 seconds of the measurement cycle, SAW devices 1 through N are alternately exposed for 15 seconds to filtered air that has passed through scrubber 132, and then for 15 seconds to ambient air that has bypassed the scrubber through line 133; the measurement cycle starts with exposure of the devices to filtered air. The flow rate through the SAW devices during this time is maintained at approximately 100 standard cubic centimeters per minute. During the 15-second intervals that the SAW devices 1 through N are exposed to ambient air, any relatively high concentration of chemical vapor in the ambient air is detected and identified by microcomputer control 186 in response to the data output from each of the SAW devices. Concurrently with the alternating 15-second intervals described above, ambient air can be drawn in parallel flow through optional concentrator 138 and exhausted to atmosphere at a flow rate of approximately 20 standard liters per minute, by pump 145 (or by pump 168, if configured as described above).

Between 105 seconds and 110 seconds after the start of the measurement cycle, pump 145 is de-energized and three-way solenoid valve 142 is closed, interrupting flow from optional concentrator 138 into line 135. In addition, solenoid valve 128 is closed and pump 168 is de-energized. Microcomputer control 186 also energizes power source 206 at its higher output current for about 5 seconds to rapidly heat wire 200 to a temperature of approximately 80° C. Thereafter, the lower output current from power source 206 is enabled to maintain the wire at that elevated temperature. Assuming an absorption enthalpy of 40 kilojoules/mole, 98% of a chemical vapor previously absorbed into polymer coating 202 on wire 200 is caused to desorb from the polymer coating by the elevated temperature.

At 110 seconds into the measurement cycle, solenoid valve 126 is opened, three-way solenoid valve 142 is switched to connect the output of optional concentrator 138 to line 135, and pump 168 is restarted. During the last 10 seconds of the measurement cycle, SAW devices 1 through N are exposed to concentrated chemical vapor desorbed from polymer coating 202, enabling microcomputer control 186 to identify and determine the ambient concentration of the chemical vapor. Flow orifice 210 in line 134 restricts the flow rate of concentrated chemical vapor into the SAW devices to about 100 standard cubic centimeters per minute. Identification of a chemical vapor and determination of its ambient concentration should be completed in a slightly longer time than that required to run the concentrator, i.e., within about 20 seconds. For some known chemical vapor/polymer coating combinations, concentrations of a chemical vapor in ambient air of less than $5 \times 10^{-4}$ milligrams per meter$^3$ can be analyzed in this time frame, for example, dimethyl methylphosphonate and fluoropolyol.

In applications where rapid identification of a chemical substance is important, it may not be practical to wait for the concentration of chemical vapor absorbed into a selected polymer coating on the SAW devices to reach its full equilibrium concentration before attempting to identify it. For example, high ambient chemical vapor concentrations may vary quickly completely saturate the polymer coating rendering the SAW device unusable for an excessive period of time. Perhaps more significantly, for very low concentrations of a chemical vapor in ambient air, achieving an equilibrium concentration of the chemical vapor in the polymer coating may require from 10 to 20 minutes of exposure to the substance. Accordingly, one of the more important aspects of the present invention provides for prediction of the equilibrium concentration of the chemical vapor within the polymer coating of a SAW device and prediction of its time constant for diffusion into the polymer coating in advance of the time at which the equilibrium concentration of the chemical vapor substance within the polymer is achieved. By quickly predicting the equilibrium concentration and time constant for diffusion of a chemical substance into the polymer coating of a SAW device, the substance may be identified much earlier in time than would otherwise be possible.

Figure 8:
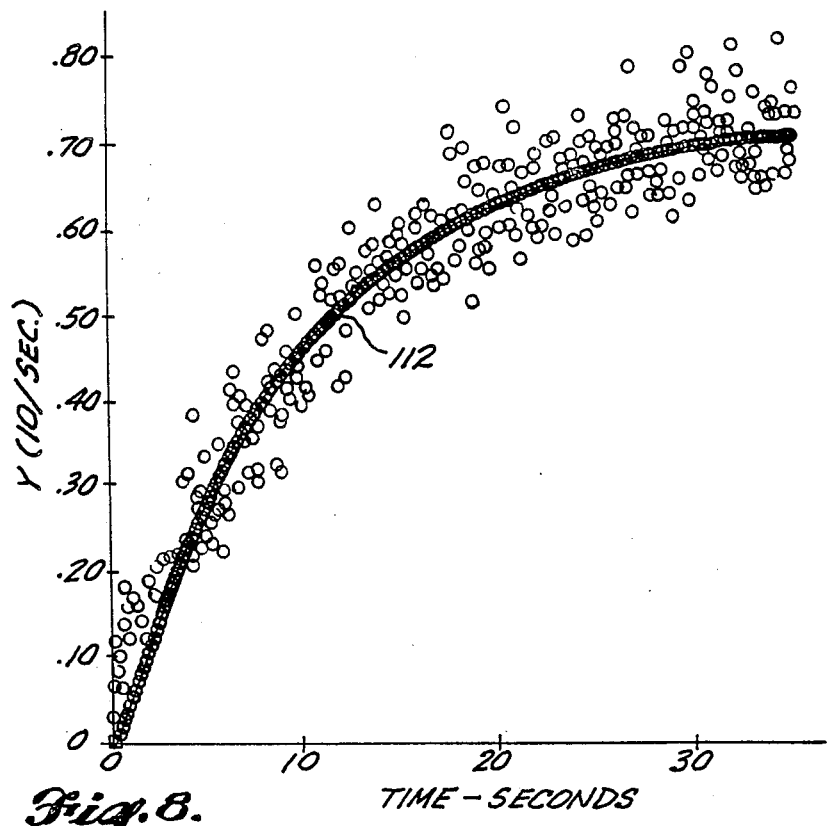
FIG. 8 is a graph showing both experimental and calculated normalized frequency data (with respect to time) for a SAW device exposed to a chemical vapor.

In FIG. 8, normalized data representing the change in resonant frequency as a function of time for a SAW device including a polymer coating of fluoropolyol is plotted using circles to represent each measurement, taken at the rate of 10 per second, as the SAW device was exposed to methyl salicylate vapor at an ambient air concentration of about 100 mg/m$^3$. An exponential curve 112 was calculated from the experimental data using a Kalman filter technique, permitting the early prediction of the equilibrium concentration of the chemical vapor in the polymer coating and of the time constant for diffusion of the chemical vapor into the polymer coating. The final normalized values for equilibrium concentration and the time for diffusion constant for curve 112 are respectively, 0.67 and 3.1.

Figure 9:
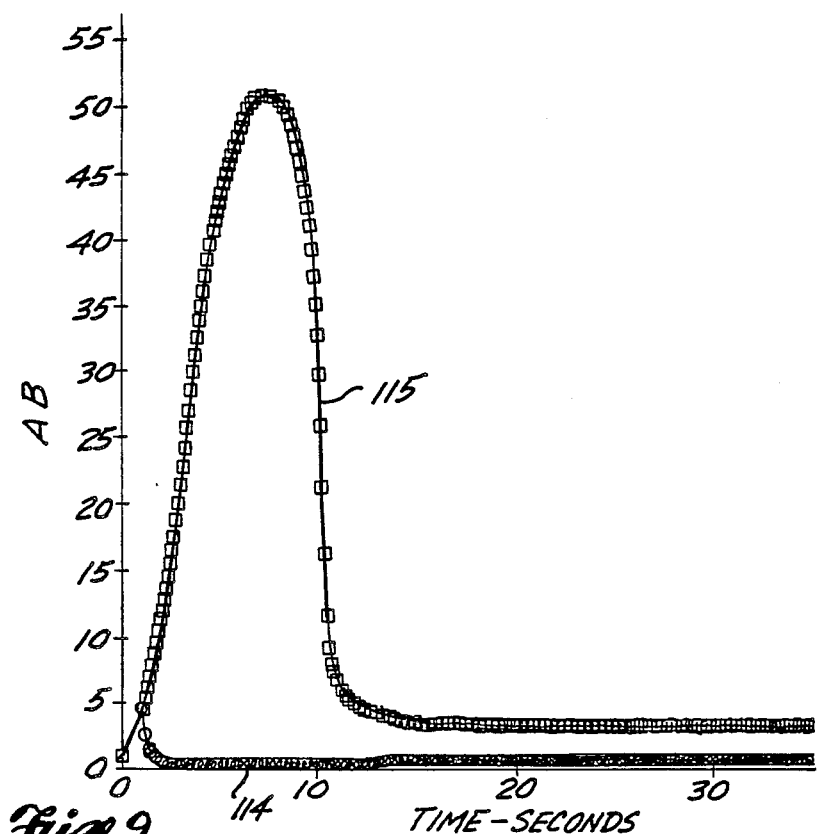
FIG. 9 is a graph showing predicted values for coefficients related to equilibrium concentration and time constant for diffusion of a chemical vapor into the polymer coating of the SAW device of FIG. 8, calculated using a Kalman filter method.

In FIG. 9, two coefficients, A and B, of an equation describing an exponential curve are predicted by the Kalman filter technique, and are plotted respectively on curves 114 and 115. The equation is defined as follows:

$$M = 0.9A(1-e^{Kt})[(1-e^{-Bt}) + 1/9(1-e^{-9Bt})] \qquad (1)$$

where

M is the mass/unit area of chemical vapor absorbed by the polymer coating;

t is the time that the polymer coating is exposed to the chemical substance;

A is the equilibrium absorption/unit area of the chemical substance in the polymer coating;

B* is the rate constant, which is related to a diffusion coefficient of the chemical substance and is the reciprocal of the time constant for diffusion, $\tau$; and K is a constant that depends on the rate of flow of the chemical substance over the polymer coating.

*for an ideal smooth coating of thickness h, A=Syh, where S is the sensitivity factor relating the equilibrium concentration within the polymer coating, X, to the concentration of the chemical substance in the vapor phase, Y, where S=X/Y; and, B=$\pi^2$D/4h, where D is the diffusion coefficient for the chemical substance in the polymer coating.

The circles and squares respectively shown on curves 114 and 115 reflect the convergence if the predicted values for coefficients A and B, where the coefficients are respectively representative of the equilibrium concentration and time constant for diffusion for the data shown in FIG. 8. It will be apparent that the predicted coefficient, A, representing equilibrium concentration, i.e., curve 114, stabilized at a relatively constant normalized value of about 0.7 within approximately three seconds after the SAW device was first exposed to the methyl salicylate vapor. However, the predicted value for the rate constant B, i.e., curve 115, took approximately 15 seconds, or about 85% of the time required for the methyl salicylate to reach equilibrium concentration in the polymer coating, to converge within 30% of the final value.

Since the Kalman filter technique of optimal estimation is well known to those skilled in the art, details are not presented herein. The procedure is documented in Section 12.4 of Chapter 12, *Applied Optimal Control*, by Bryson and Ho. Although the relatively long period of time required to predict the value of coefficient B in the above example limits its usefulness, the Kalman filter technique for predicting equilibrium concentration and time constant for diffusion of a chemical substance into a polymer coating would nevertheless permit discrimination of one chemical substance from another prior to the time that full equilibrium concentration in the polymer coating is achieved.

Figure 10:
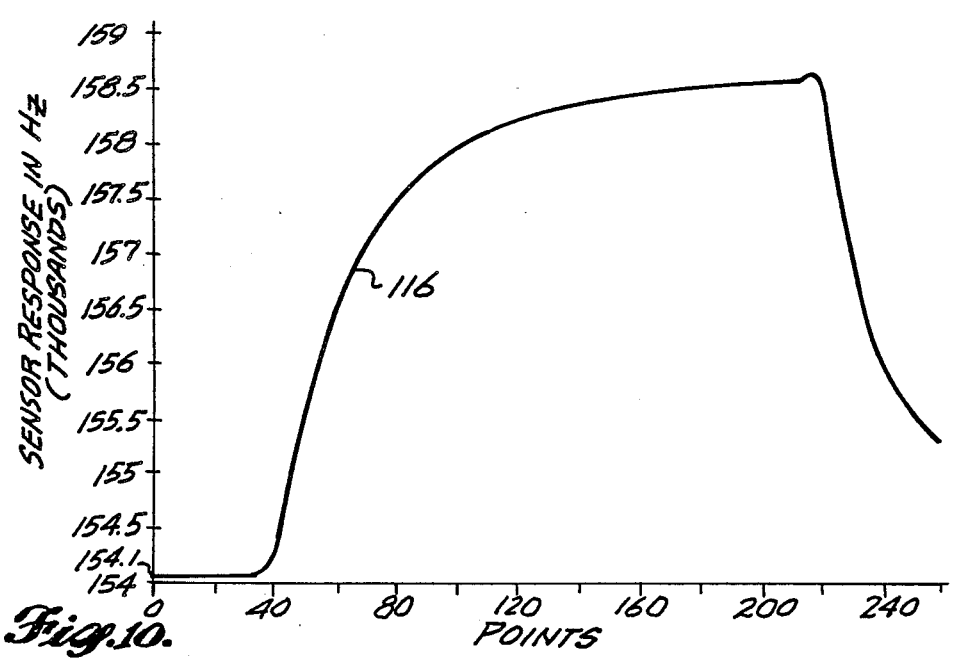
FIG. 10 is a graph showing the resonant frequency of a SAW device exposed to methyl salicylate vapor as a function of the number of sampling points (i.e., over time)

A curve 116 representing the change in frequency for a succession of data points taken at the rate of approximately 10 per second is shown in FIG. 10 for a SAW device having a fluoropolyol polymer coating, as the SAW device is exposed to a relatively low ambient air concentration of methyl salicylate vapor. Curve 116 is an exponential curve that changes in time as the methyl salicylate vapor is absorbed into the fluoropolyol on the SAW sensor. The increase in mass of the polymer coating due to the absorption of the methyl salicylate vapor causes a change in the difference frequency of the SAW device from its initial value of 154.1 kilohertz, asymptotically achieving an equilibrium value of approximately 158.6 kilohertz. After approximately 220 data points were sampled, the flow of methyl salicylate vapor into the SAW device was terminated, and the mass of the methyl salicylate within the polymer coating thereafter decreased by desorption.

Figure 11:
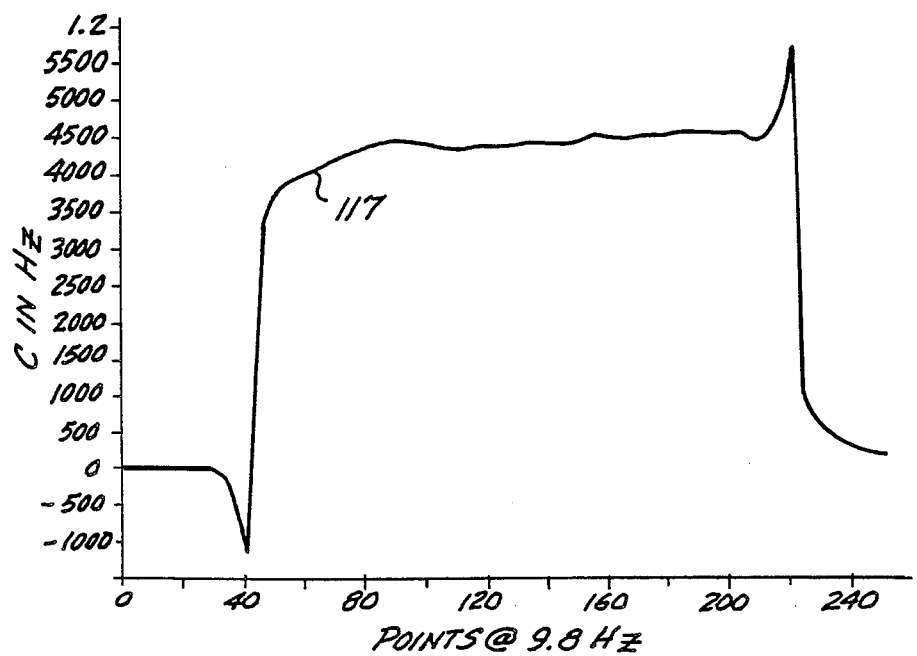
FIG. 11 is a graph showing the predicted equilibrium concentration of methyl salicylate within the polymer coating of the SAW device, for the data shown in FIG. 10.
Figure 12:
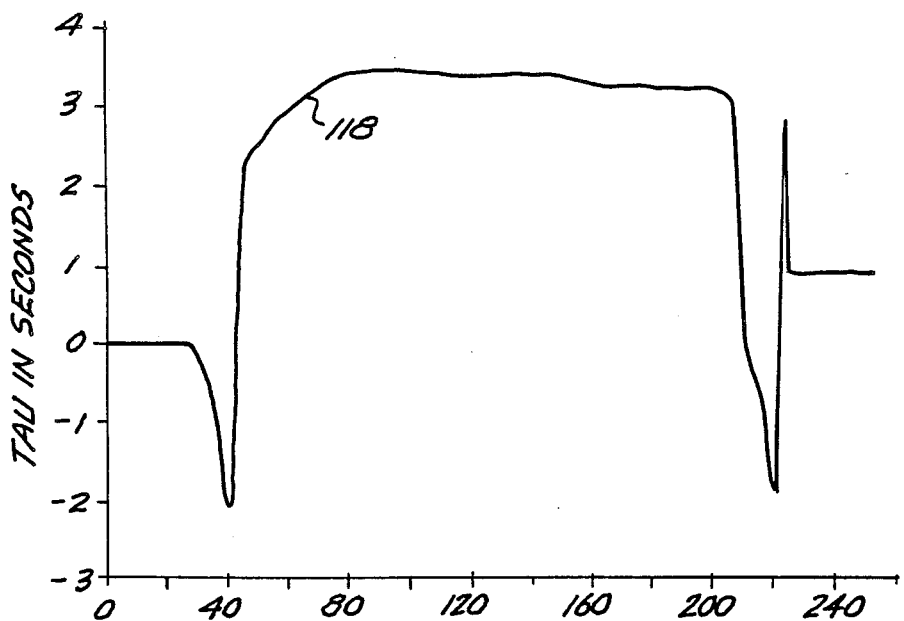
FIG. 12 is a graph showing the predicted rate constant for diffusion of methyl salicylate within the SAW device, for the data shown in FIG. 10.

In FIG. 11, the method described in the referenced co-pending application was applied to the data of FIG. 10, producing a curve 117, which defines the predicted equilibrium concentration of the methyl salicylate vapor within the fluoropolyol coating as a function of the number of data points. In FIG. 11, the equilibrium concentration is expressed in terms of the change in frequency, C, caused by the change in mass due to the absorption of the methyl salicylate. Similarly, in FIG. 12, a prediction for the time constant for diffusion, $\tau$, of the methyl salicylate vapor into the fluoropolyol as a function of the number of data points is presented by a curve 118. Both curves 117 and 118 achieve predicted values for C and $\tau$, respectively, that are within about 30% of final values in less than 10% of the time required for the methyl salicylate to reach its equilibrium concentration. A much more accurate prediction is achieved within about ½ of that time. Thus, it should be apparent that this method provides a relatively accurate and fast prediction of the final equilibrium concentration and time (or rate) constant for diffusion of a chemical vapor into a polymer coating, which may be used to identify the chemical vapor and to determine its concentration in ambient air much sooner than would otherwise be possible for relatively low concentrations of the chemical vapor.

Regardless of which method is used to provide the values for equilibrium concentration and time constant for diffusion, once the chemical vapor is identified using those characteristic parameters, its ambient concentration is determined by comparing its predicted equilibrium concentration in the polymer coating to calibration data for the SAW device with respect to that particular chemical vapor. The calibration data for each chemical vapor of interest is stored in the memory of microcomputer control 186; these data relate various equilibrium concentrations of the chemical vapors to their calibrated ambient air concentrations, so that ambient air concentration may be extrapolated from the predicted equilibrium concentration. The use of predicted values for the two characteristic parameters of the diffusion enable the ambient concentration of the chemical vapor to be rapidly determined with an accuracy of about ±30%.

Although the chemical sensor described for use with the preferred embodiment of the present invention is a SAW device, it should be apparent that any chemical sensor having a physical parameter that changes with the absorption of a chemical substance into a material coating the sensor could be used to provide data concerning the rate of change or time constant for the change of the physical parameter, in addition to the equilibrium concentration of the chemical vapor within the material coating. Prediction of the final equilibrium concentration of the chemical vapor within the material coating of the chemical sensor and prediction of the time constant for diffusion therein is equally applicable to these other types of chemical sensors. For example, a chemical field effect transistor (CHEMFET) includes conventional source and drain electrodes and a gate region coated with a layer of a polymer, e.g., one of the polymers described above as being suitable for use with SAW device 10. Absorption of a chemical substance by the polymer layer causes the electric field beneath the gate to change as a function of the mass of the chemical substance absorbed by the polymer. Change of the electric field due to the absorption of the chemical substance modulates the flow of free charge carriers within the CHEMFET, controlling the conductivity between its source and drain junctions.

Furthermore, the chemical sensor used in the present invention may comprise a chemical resistor, which changes impedance due to the absorption of a chemical substance in a material coating a surface of the device. As a chemical substance diffuses into the material coating, the resistance of the chemical resistor changes proportionally. Both the CHEMFET and the chemical resistor are well known to those of ordinary skill in this art and details of their structure need not be shown herein. In any case, the SAW device is the preferred chemical sensor, since it is more sensitive to relatively low concentrations of chemical substance than are the other types of chemical sensors described above. It should also be apparent that the present invention is not limited to detecting, identifying, and determining the ambient concentration of chemical vapors, but is also usable in a similar fashion for detecting and identifying chemical substances in other forms, such as particulate matter, liquids, aerosol sprays, permanent gases, and in fact may be used to identify any form of chemical substance that diffuses into the polymer coating of a chemical sensor.

While the present invention has been described with respect to preferred embodiments and modifications thereto, it will be understood by those of ordinary skill in the art that further modifications may be made within the scope of the claims that follow. Accordingly, the scope of the invention is not to be in any way limited by the disclosure of the preferred embodiments, but should be determined entirely by reference to the claims.

The embodiments of the invention in which an exclusive property or privilege is claimed are defined as follows:

1. Apparatus for rapidly detecting and identifying a chemical substance, comprising:
    (a) a sensor having a surface exposed to the chemical substance and comprising a material selectively absorptive of a group of chemical substances of which said chemical substance is a member, a physical parameter associated with that surface changing as the quality of the chemical substance absorbed by diffusion into the material changes;
    (b) monitoring means, coupled to the sensor, for monitoring the change in the physical parameter associated with said surface due to absorption of the chemical substance, producing an electrical signal indicative of said charge;
    (c) analysis means, connected to the monitoring means, for determining a predicted time constant for diffusion of the chemical substance into the material and a predicted equilibrium concentration of the chemical substance in the material as a function of the electrical signal, well before the concentration of the chemical substance in the material asymptotically approaches equilibrium; and
    (d) identification means for identifying the chemical substance from said group of chemical substances based on both its predicted time constant for diffusion and predicted equilibrium concentration, which are generally characteristic of the chemical substance and different than those of other chemical substances of the group.

2. The apparatus of claim 1, wherein the identification means are further operative to determine the approximate concentration of the chemical substance in a sample of air to which the material is exposed, as a function of its predicted time constant for diffusion into the material and its predicted equilibrium concentration in the material.

3. The apparatus of claim 1, wherein the sensor comprises a surface acoustic wave device having at least one surface coated with the material selectively absorptive of the group of chemical substances, absorption of said chemical substance into said material changing its mass, said physical parameter comprising the frequency of a surface acoustic wave propagating along the coated surface of the surface acoustic wave device, said frequency decreasing as the mass of the coating increases due to absorption of the chemical substance.

4. The apparatus of claim 3, wherein the material coating said at least one surface of the surface acoustic wave device comprises a polymer.

5. The apparatus of claim 3, wherein a plurality of spaced apart electrodes are disposed on said at least one surface of the surface acoustic wave device, with the material disposed between pairs of the electrodes, said apparatus further comprising means to excite the surface acoustic wave device with a periodically varying signal.

6. The apparatus of claim 5, wherein the monitoring means comprise a high speed counter connected to determine the frequency of the surface acoustic wave propagating through the material, at a sampling rate that is substantially faster than an expected time for the concentration of chemical substance in the material to reach equilibrium, said electrical signal indicating the change in frequency due to absorption of the chemical substance in the material coating said at least one surface of the acoustic wave device.

7. The apparatus of claim 1, wherein the analysis means comprise a Kalman filter for determining the predicted time constant for diffusion of the chemical substance into said material and the predicted equilibrium concentration of the chemical substance in said material according to an approximation based on:

$$M = 0.9A(1-e^{-Kt})[(1-e^{-Bt}) + 1/9(1-e^{-9Bt})]$$

where
- M = the mass/unit area of chemical substance absorbed by the material;
- t = time that material is exposed to the chemical substance;
- A = the equilibrium absorption/unit area of chemical substance;
- B = a rate constant, which is related to a chemical substance diffusion coefficient and is the reciprocal of the time constant for diffusion; and
- K = a constant that depends on rate of flow of chemical substance over the material coating.

8. The apparatus of claim 1, wherein the analysis means are operative to determine the predicted time constant for diffusion and the predicted percent of the time required for the concentration of chemical substance in the material to reach equilibrium.

9. The apparatus of claim 1, further comprising a chemical substance concentrator, for increasing the relative concentration of the chemical substance to which the surface is exposed.

10. The apparatus of claim 1, wherein the identification means comprise logic means for comparing the predicted time constant for diffusion and predicted equilibrium concentration determined by the analysis means to those listed in a look-up table identifying specific members of the group of chemical substances as a function of their characteristic time constant for diffusion and equilibrium concentration in said material.

11. The apparatus of claim 1, further comprising a plurality of other sensors, each having a surface exposed to the chemical substance and each comprising a different material selectively absorptive of a different group of chemical substances, said identification means being operative to identify the chemical substance as a function of predicted rates of diffusion and predicted equilibrium concentrations determined by the analysis means for all of the sensors.

12. The apparatus of claim 1, wherein the sensor comprises a chemical field effect transistor including a semiconductor coated with the material, the diffusion of chemical substance into the material modulating the flow of free charge carriers therewithin, said physical parameter comprising the conductivity between a source and a drain of the chemical field effect transistor due to a localized field in the material caused by absorption of the chemical vapor.

13. The apparatus of claim 1, wherein the sensor comprises a chemical resistor which changes impedance as the chemical substance diffuses into the material, and wherein the physical parameter comprises the resistance of the chemical resistor.

14. A method for detecting and identifying a particular chemical substance from a group of chemical substances, comprising the steps of:
(a) exposing a surface to the chemical substance, said surface comprising a material selectively absorptive of said group of chemical substances;
(b) sensing a physical parameter associated with the surface, which changes due to absorption of the chemical substance by the material comprising said surface;
(c) producing an electrical signal indicative of the change in the physical parameter associated with said surface due to absorption of the chemical substance;
(d) determining a predicted time constant for diffusion of the chemical substance into the surface and a predicted equilibrium concentration of the chemical substance within the material as a function of the electrical signal, well before the concentration asymptotically reaches equilibrium; and
(e) identifying the chemical substance from said group of chemical substances, based on both its predicted time constant for diffusion and predicted equilibrium concentration, which are generally characteristic of the chemical substance and different than those of other chemical substances of the group.

15. The method of claim 14, further comprising the step of determining the approximate concentration of the chemical substance in a sample of air to which the material is exposed, as a function of its predicted time constant for diffusion into the material and its predicted equilibrium concentration in the material.

16. The method of claim 14, wherein a surface acoustic wave device has at least one surface coated with the material selectively absorptive of the group of chemical substances, absorption of the chemical substance into the material changing its mass, said physical parameter comprising the frequency of a surface acoustic wave propagating along the coated surface of the surface acoustic wave device, said frequency decreasing as the mass of the coating increases due to absorption of the chemical substance.

17. The method of claim 16, wherein the material coating said at least one surface of the surface acoustic wave device comprises a polymer.

18. The method of claim 16, wherein a plurality of spaced apart electrodes are disposed on said at least one surface of the surface acoustic wave device, with the material disposed between pairs of the electrodes, further comprising the step of exciting said pairs of electrodes with a periodically varying signal.

19. The method of claim 18, wherein the step of sensing the physical parameter comprises the step of determining the frequency of the surface acoustic wave propagating through the material, at a sampling rate that is substantially faster than an expected time for the concentration of chemical substance in the material to reach equilibrium, and wherein the electrical signal indicates the change in frequency due to absorption of the chemical substance in the material coating said at least one surface of the acoustic wave device.

20. The method of claim 14, wherein a Kalman filter is used for determining the predicted time constant for diffusion and the predicted equilibrium concentration of the chemical substance in said material according to an approximation based on:

$$M = 0.9A(1-e^{-Kt})[(1-e^{-Bt}) + 1/9(1-e^{-9Bt})]$$

where
- M = the mass/unit area of chemical substance absorbed by the material;
- t = time that material is exposed to the chemical substance;

A = the equilibrium absorption/unit area of chemical substance;

B = a rate constant, which is related to a chemical substance diffusion coefficient and is the reciprocal of the time constant for diffusion; and K = a constant that depends on rate of flow of the chemical substance over the material coating.

21. The method of claim 14, wherein the step of determining the predicted time constant for diffusion and the predicted equilibrium concentration of the chemical substance in the material is completed in about ten percent of the time required for the concentration of chemical substance in the material to reach equilibrium.

22. The method of claim 14, further comprising the step of increasing the relative concentration of chemical substance to which the surface is exposed.

23. The method of claim 14, wherein the step of identifying the chemical substance comprises the step of comparing the predicted time constant for diffusion and the predicted equilibrium concentration with those listed in a look-up table identifying specific members of the group of chemical substances as a function of their characteristic time constant for diffusion and equilibrium concentration in said material.

24. The method of claim 14, further comprising the step of exposing other surfaces comprising different materials that are each selectively absorptive of a group of chemical substances, determining the predicted rates of diffusion and predicted equilibrium concentrations of the chemical substance in the materials of each of the other surfaces, and identifying the chemical substance as a function of all the predicted rates of diffusion and predicted concentrations of the chemical substance in the materials comprising all the surfaces.

25. The method of claim 14, wherein the physical parameter comprises the conductivity between a source and a drain of a chemical field effect transistor that includes the material into which the chemical substance diffuses, thereby modulating the flow of free charge carriers between the source and drain.

26. The method of claim 14, wherein the physical parameter comprises the resistance of a chemical resistor.

27. A method for rapidly identifying an unknown chemical substance that is one of a group of chemical substances, comprising the steps of:
(a) exposing the chemical substance to a surface of a sensor that includes a material selected for its affinity to absorb a chemical substance from said group of chemical substances, said sensor effecting an electrical signal that changes as the chemical substance diffuses into the material as a function of the quantity of the chemical substance absorbed therein;
(b) monitoring the sensor for changes in the electrical signal indicative of the diffusion of the chemical substance into the material;
(c) predicting the time constant for diffusion of said chemical substance into the material of the sensor and its equilibrium concentration in the material, at a time substantially prior to chemical substance reaching its equilibrium concentration in the material; and
(d) identifying the chemical substance as a function of both its predicted time constant for diffusion and its predicted equilibrium concentration in the material of the sensor.

28. The method of claim 27, further comprising the step of determining the approximate concentration of the chemical substance in a sample as a function of its predicted time constant for diffusion and predicted equilibrium concentration in the material.

29. The method of claim 27, wherein the material of the sensor is absorptive of other chemical substances from the group of chemical substances, the step of identifying the chemical substance as a function of its predicted time constant for diffusion and equilibrium concentration comprising the step of stochastically selecting a most probable chemical substance having a characteristic time constant for diffusion and equilibrium concentration in the material substantially the same as the predicted time constant for diffusion and predicted equilibrium concentration.

30. The method of claim 29, further comprising the steps of:
(a) exposing surfaces of other sensors, each including different materials selected for their ability to absorb chemical substances from different groups of chemical substances, said sensors effecting electrical signals that change as a function of the quantity of chemical substances absorbed therein;
(b) monitoring the other sensors for changes in their electrical signals indicative of the diffusion of the chemical substances into their respective different materials;
(c) predicting the rates of chemical diffusion of the chemical substances into the different materials, at a time substantially prior to their reaching equilibrium concentration; and
(d) identifying the chemical substance as a function of the predicted rates of diffusion and predicted equilibrium concentration in the materials of all the sensors.

* * * * *

UNITED STATES PATENT AND TRADEMARK OFFICE
CERTIFICATE OF CORRECTION

PATENT NO. : 4,895,017  
DATED : January 23, 1990  
INVENTOR(S) : Pyke et al.

Page 1 of 2

It is certified that error appears in the above-identified patent and that said Letters Patent is hereby corrected as shown below:

| Column | Line(s) | |
|---|---|---|
| Section [56], 2nd Reference | | "Mueller" should be --Muller-- |
| 1 | 55 | "chemically" should be --chemically-- |
| 1 | 58 | "physically" should be --physically-- |
| 2 | 14 & 15 | "Analytical Chemistry" should be --Analytical Chemistry-- |
| 5 | 44 | "not" should be --not-- |
| 6 | 24 | "and" should be --an-- |
| 6 | 34 | "the" should be --that-- |
| 6 | 37 | After "Lead 64" insert the word --is-- |
| 6 | 41 | "lead" should be --leads-- |
| 7 | 27 | "time for diffusion" should be --time for diffusion-- |
| 7 | 59 | "both" should be --both-- |
| 7 | 65 | "only" should be --only-- |
| 10 | 59 | "rapid" should be --rapid-- |
| 11 | 11 | "predicting" should be --predicting-- |

UNITED STATES PATENT AND TRADEMARK OFFICE
CERTIFICATE OF CORRECTION

PATENT NO. : 4,895,017

DATED : January 23, 1990

INVENTOR(S) : Pyke et al.

It is certified that error appears in the above-identified patent and that said Letters Patent is hereby corrected as shown below:

| Column | Line(s) | |
|---|---|---|
| 11 | 51 | "A=Syh" should be --A=SYh-- |
| 11 | 55 | "if" should be --of-- |
| 13 | 7 | After the word "diffusion" insert the word --process-- |
| 14<br>Claim 1, line 14 | 14 | "charge" should be --change-- |
| 17<br>Claim 24, line 2 | 26 | "step" should be --steps-- |
| 18<br>Claim 30, line 4 | 35 | "ability" should be --affinity-- |

Signed and Sealed this

Ninth Day of April, 1991

*Attest:*

HARRY F. MANBECK, JR.

*Attesting Officer*     *Commissioner of Patents and Trademarks*